United States Patent [19]

Russell

[11] Patent Number: 5,060,645

[45] Date of Patent: Oct. 29, 1991

[54] TRACHEOSTOMY TUBE ASSEMBLY

[76] Inventor: David N. Russell, 9737-123rd Street, Surrey, Canada, V3V 4N7

[21] Appl. No.: 567,097

[22] Filed: Aug. 14, 1990

[51] Int. Cl.$^5$ ............................................... A62B 9/04
[52] U.S. Cl. ......................... 128/207.14; 128/207.17; 128/207.29; 128/200.26
[58] Field of Search ............... 128/207.14, 207.17, 128/207.29, 200.26; 604/174–180, 338

[56] References Cited

U.S. PATENT DOCUMENTS

| | | | |
|---|---|---|---|
| 1,835,757 | 12/1931 | Burchett | 128/207.17 |
| 3,225,767 | 12/1965 | Smith | 128/200.26 |
| 4,223,671 | 9/1980 | Muto | 128/200.26 |
| 4,235,229 | 11/1980 | Ranford et al. | 128/207.17 |
| 4,331,144 | 5/1982 | Wapner | 128/207.17 |
| 4,489,723 | 12/1984 | Simons et al. | 128/207.16 |
| 4,583,977 | 4/1986 | Shishov et al. | 128/DIG. 26 |
| 4,649,913 | 3/1987 | Watson | 604/174 |
| 4,732,147 | 3/1988 | Fuller | 128/207.18 |
| 4,877,025 | 10/1989 | Hanson | 128/204.16 |

Primary Examiner—Edgar S. Burr
Assistant Examiner—Lisa Malvaso
Attorney, Agent, or Firm—Jerry T. Kearns

[57] ABSTRACT

A tracheostomy tube assembly comprises a tracheostomy tube and a separate collar member which can be removably attached to the tube. The collar member is fastenable around a patient's neck by flexible fastening means. The collar member can be removed from the tube for attaching the flexible fastening means thereto.

14 Claims, 1 Drawing Sheet

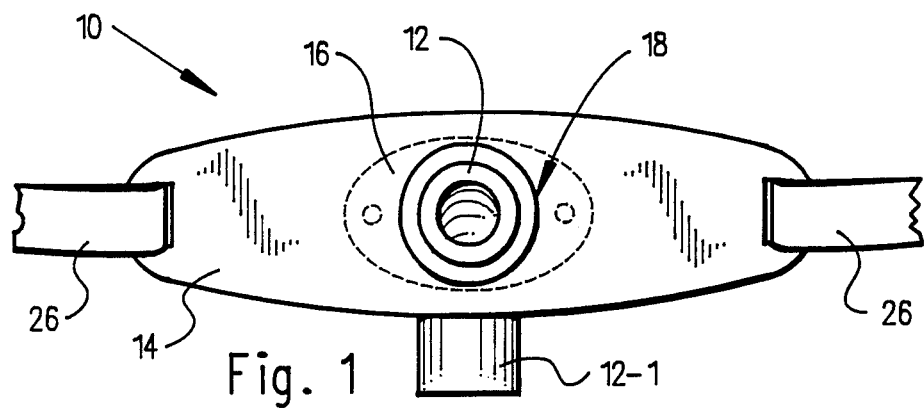
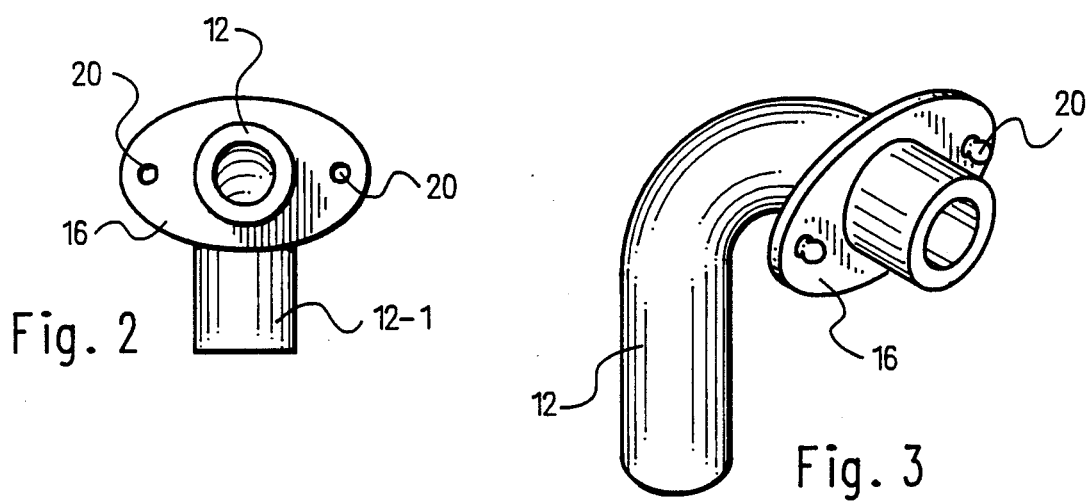
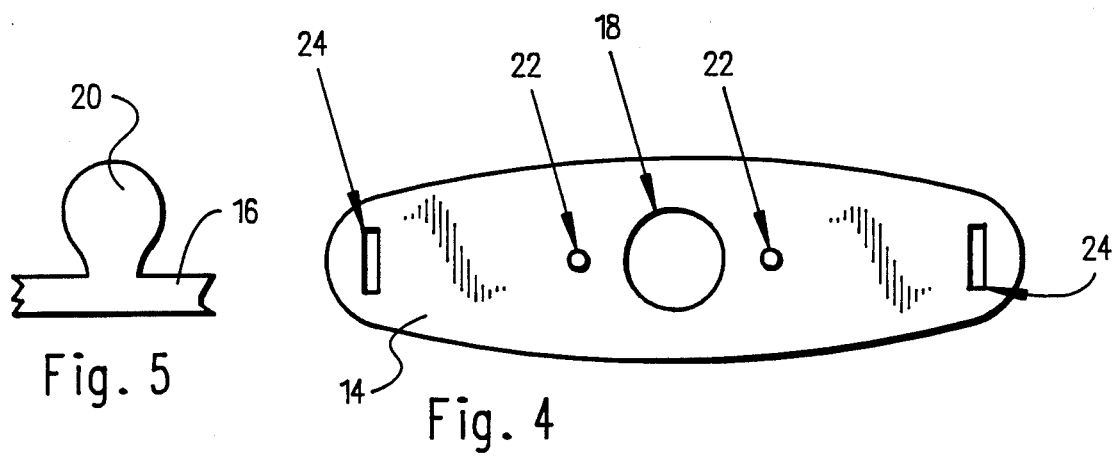

TRACHEOSTOMY TUBE ASSEMBLY

INTRODUCTION

This invention relates to a tracheostomy tube assembly, as well as a tracheostomy tube and a collar member for use in the assembly.

BACKGROUND OF THE INVENTION

Tracheostomy tubes and endotracheal tubes are usually supported in place by thin cotton tape which extends around the neck of a patient. The ends of the tape tie to openings which are provided in a flange on the tube. The cloth tape or ties require periodic replacing due to soiling from the wound and other causes. During replacement, the replacement tape has to be threaded through the openings in the flanges on the tracheostomy tube whilst the tube is in place on a patient's throat. This operation usually needs to be carried out in front of a mirror and is time consuming and often difficult for a patient to carry out, especially for young children and elderly patients. It is particularly a problem where the patient has already been discharged from hospital and is required to change the ties at home where no nursing assistance is available.

SUMMARY OF THE INVENTION

According to the invention, there is provided a tracheostomy tube assembly which comprises a tracheostomy tube having one end adapted for insertion into the trachea through a stoma cut in a patient's throat and a separate collar member adapted to be fitted on the exterior of the throat for supporting the tube in place and having an opening for receiving the tracheostomy tube therethrough, and which collar member is removably attachable to the tube. Conveniently, the tracheostomy tube is provided with a flange for resting against the collar member when the tracheostomy tube is inserted through the opening in the collar member and means is included for releasably fastening the flange to the collar member. Thus, by providing a separate collar member which is removable from the tracheostomy tube, the ties can be inserted when the collar member is removed from the patient's throat, thus rendering the exchanging of ties easy and quick.

Also according to the invention, there is provided a collar member for use in a tracheostomy assembly which is adapted to be fitted on the exterior of a patient's throat and having an opening for receiving a tracheostomy tube therethrough and including means for releasably fastening the collar member to a tracheostomy tube.

Further according to the invention, there is provided a tracheostomy tube for use in a tracheostomy assembly having one end adapted for insertion into the trachea through a stoma cut in a patient's throat and wherein the tube is provided with a flange for resting against a separate collar member when the tracheostomy tube is inserted through the hole in the collar and including means for releasably fastening the flange to the collar.

Also according to the invention, there is provided a collar for use in a tracheostomy tube assembly, comprising a collar member which is adapted to be fitted on the exterior of a patient's throat and having an opening for receiving a tracheostomy tube therethrough and including means for releasably fastening the collar member to a tracheostomy tube, and a flexible fastening means connected to the collar for fastening the collar around a patient's neck.

Further objects and advantages of the invention will become apparent from the description of a preferred embodiment of the invention below.

DESCRIPTION OF THE DRAWINGS

The invention will now be described, by way of an example, with reference to the accompanying drawings, in which:

FIG. 1 is a front view of a tracheostomy tube assembly according to the invention;

FIG. 2 is a front view of a tracheostomy tube of the assembly of FIG. 1;

FIG. 3 is a perspective view of the tracheostomy tube of FIG. 2;

FIG. 4 is a front or plan view of a collar member of the tracheostomy tube assembly of FIG. 1; and FIG. 5 is a fragmentary side view of a stud of the collar member of FIG. 4.

DETAILED DESCRIPTION

With reference to FIG. 1, reference numeral 10 generally indicates a tracheostomy tube assembly comprising a tracheostomy tube 12 and a separate collar member 14 for use with the tube 12.

The tracheostomy tube 12 has an end 12.1 which is adapted for insertion into the trachea through a stoma cut in a patient's throat. The tube 12 is further provided with a flange 16. The collar member 14 is adapted to be fitted on the exterior of the throat of a patient and it has an opening 18 for receiving the tracheostomy tube 12 therethrough. The flange 16 rests against the collar member 14 when the tracheostomy tube 12 is inserted through the opening 18 in the collar member 14.

Means for releasably fastening the flange 16 to the collar member 14 is provided. In the present example, it takes the form of a pair of studs 20 on the flange 16 (shown in enlarged view in FIG. 5) and a pair of openings 22 in the collar member 14 for receiving the studs 20. The collar member 14 further has a pair of opposite ends which are provided with slots 24 for receiving flexible fastening means, such as cotton tape 26, as shown in FIG. 1. The collar member 14 is conveniently molded from a suitable plastic material. Likewise, the tracheostomy tube 12 is also formed from a suitable plastic material. The collar member 14 may be of an inexpensive material so that it is discardable. According to one aspect of the invention, the collar member and cotton tape are provided as a disposable combination which is discarded after use.

OPERATION

When it is desired to exchange the tape 26, the patient will untie the tape 26 and remove the tape 26 and collar member 14 from the tracheostomy tube 12, while holding the tube 12 in place. This is accomplished by unclipping the collar member 14 from the studs 20 on the flange 16.

With the collar member 14 and tape 26 removed, the tape 26 can be discarded, the collar member 14 can be cleaned and a new tape 26 can be inserted through the slots 24, while the collar member 14 is removed from the tube 12. This can be very easily done because the patient will be holding the collar member 14 in front of him instead of it being around his neck and requiring the use of a mirror. Alternatively, the collar member 14 can be discarded with the tape 26 and a new collar member 14 and tape 26 can be used. If the tape 26 has not already been inserted through the slots 24 of the new collar member, it is possible for the patient to do so without the collar member 14 and tape 26 being around the neck. This is again done by a patient holding the collar member 14 and tape 26 in front of him. Once the tape 26 has been inserted through the slots 24, the tape 26 and collar member 14 is placed around the neck and the tracheostomy tube 12 is inserted through the opening 18. The studs 20 are then engaged with the openings 22 and the tape 26 is tied around the neck. It will thus be seen that this operation greatly simplifies the act of replacing the cloth tape 26 since it is no longer necessary to insert the tape through the slots in the flange of the tracheostomy tube when it is located around the neck.

The advantage of the present invention is that the user may have a fresh collar member and tape ready for fitting before removing the old collar member and tape from around the neck.

It will be appreciated that various variations from the specific embodiment described above are possible. For example, instead of using a cloth tape, VELCRO brand cooperating hook and loop-type fasteners may be employed for attaching the collar member to a band extending around the neck of a patient. In such a case, VELCRO brand strips can be used which are threaded through the openings on the opposite ends of the collar member. Apart from VELCRO brand cooperating hook and loop-type fasteners, any other suitable fastening means may be used such as a cord, a strap or a band, which is not necessarily of a cloth type material.

While only preferred embodiments of the invention have been described herein in detail, the invention is not limited thereby and modifications can be made within the scope of the attached claims.

What is claimed is:

1. A tracheostomy tube assembly comprising:
 a tracheostomy tube possessing a first end adapted for insertion into a trachea of a patient through a stoma cut in a patient's throat and a second end opposite said first end;
 a flange extending substantially radially outwardly adjacent said second end of said tracheostomy tube;
 a pair of substantially diametrically opposed studs projecting outwardly from an outer surface of said flange, said studs disposed on opposite sides of said tube;
 each of said studs having a rounded enlarged terminal end portion connected to said flange by a reduced width neck portion;
 a separate collar member adapted to be fitted on the exterior of a patient's throat, said collar member possessing an opening receiving said tracheostomy tube;
 a pair of apertures formed through said collar member, said apertures disposed on opposite sides of said opening and dimensioned for releasable engagement with said studs; and
 flexible fastening means secured to said collar member for securing said collar member around a patient's neck.

2. The tracheostomy tube assembly of claim 1, wherein said collar member possesses a pair of opposite ends provided with slots receiving said flexible fastening means therethrough.

3. The tracheostomy tube assembly of claim 2, wherein said flexible fastening means comprises discardable cloth type.

4. The tracheostomy tube assembly of claim 1, wherein said flexible fastening means comprises discardable cloth tape.

5. The tracheostomy tube assembly of claim 1, wherein said second end of said tracheostomy tube projects substantially past said outer surface of said flange such that said second end of said tracheostomy tube may be inserted through said opening in said collar member to dispose said outer surface of said flange proximate an inner surface of said collar member.

6. A tracheostomy tube assembly comprising:
 a tracheostomy tube possessing a first end adapted for insertion into a trachea of a patient through a stoma cut in a patient's throat and a second end opposite said first end;
 a flange extending substantially radially outwardly adjacent said second end of said tracheostomy tube;
 said flange possessing an inner surface adapted to lie against a patient's throat and an outer surface opposite said inner surface;
 a pair of substantially diametrically opposed studs projecting outwardly from said outer surface of said flange, said studs disposed on opposite sides of said tube;
 each of said studs having a rounded enlarged terminal end portion connected to said flange by a reduced width neck portion;
 a separate collar member adapted to be fitted on the exterior of a patient's throat, overlying said outer surface of said flange, said collar member possessing a substantially central opening receiving said tracheostomy tube therethrough;
 a pair of apertures formed through said collar member, said apertures disposed on opposite sides of said central opening and dimensioned for releasable engagement with said studs; and
 flexible fastening means secured to said collar member for releasably securing said collar member around a patient's neck, whereby said collar member may be disengaged from said flange and removed from around a patient's neck without withdrawing said tracheostomy tube from a patient's trachea.

7. The tracheostomy tube assembly of claim 6, wherein said collar member possesses a pair of opposite ends provided with slots receiving said flexible fastening means therethrough.

8. The tracheostomy tube assembly of claim 7, wherein said flexible fastening means comprises discardable cloth tape.

9. The tracheostomy tube assembly of claim 6, wherein said flexible fastening means comprises discardable cloth tape.

10. The tracheostomy tube assembly of claim 6, wherein said second end of said tracheostomy tube projects substantially past said outer surface of said flange such that said second end of said tracheostomy tube may be inserted through said central opening in said collar member to dispose said outer surface of said flange proximate an inner surface of said collar member.

11. A tracheostomy tube assembly comprising:
 a tracheostomy tube possessing a first end adapted for insertion into a trachea of a patient through a stoma cut in a patient's throat and a second end opposite said first end;

a flange extending substantially radially outwardly adjacent said second end of said tracheostomy tube;

said flange possessing an inner surface adapted to lie against a patient's throat and an outer surface opposite said inner surface;

a pair of substantially diametrically opposed studs projecting outwardly from said outer surface of said flange, said studs disposed on opposite sides of said tube;

each of said studs having a rounded enlarged terminal end portion connected to said flange by a reduced width neck portion;

a separate collar member adapted to be fitted on the exterior of a patient's throat, overlying said outer surface of said flange, said collar member possessing a substantially central opening receiving said tracheostomy tube therethrough;

a pair of apertures formed through said collar member, said apertures disposed on opposite sides of said central opening and dimensioned for releasable engagement with said studs, such that said collar member may be selectively captured in a region of the reduced neck portion of said studs, between said outer surface of said flange and said enlarged terminal end portions of said studs;

said second end of said tracheostomy tube projecting substantially past said outer surface of said flange such that said second end of said tracheostomy tube may be inserted through said central opening in said collar member to dispose said outer surface of said flange proximate an inner surface of said collar member; and flexible fastening means secured to said collar member for releasably securing said collar member around a patient's neck, whereby said collar member may be disengaged from said flange and removed from around a patient's neck without withdrawing said tracheostomy tube from a patient's trachea.

12. The tracheostomy tube assembly of claim 11, wherein said collar member possesses a pair of opposite ends provided with slots receiving said flexible fastening means therethrough.

13. The tracheostomy tube assembly of claim 12, wherein said flexible fastening means comprises discardable cloth tape.

14. The tracheostomy tube assembly of claim 11, wherein said flexible fastening means comprises discardable cloth tape.

* * * * *